United States Patent
Mishima

(10) Patent No.: US 10,520,014 B2
(45) Date of Patent: Dec. 31, 2019

(54) ABNORMAL WEARING DETECTION DEVICE FOR SEAL MEMBERS AND ROTOR DEVICE

(71) Applicant: FANUC CORPORATION, Yamanashi (JP)

(72) Inventor: Yamato Mishima, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 0 days.

(21) Appl. No.: 15/971,110

(22) Filed: May 4, 2018

(65) Prior Publication Data

US 2018/0363698 A1 Dec. 20, 2018

(30) Foreign Application Priority Data

Jun. 19, 2017 (JP) ................................. 2017-119277

(51) Int. Cl.
*F16C 17/24* (2006.01)
*G01M 13/005* (2019.01)
(Continued)

(52) U.S. Cl.
CPC ............ *F16C 17/246* (2013.01); *F16C 17/02* (2013.01); *F16J 15/00* (2013.01); *F16J 15/3296* (2013.01);
(Continued)

(58) Field of Classification Search
CPC ..... F16C 17/246; F16C 17/02; G01M 13/005; G01M 3/002; F16J 15/3296; F16J 15/00; G01N 3/56; F01D 25/186; F01D 21/12
See application file for complete search history.

(56) References Cited

U.S. PATENT DOCUMENTS 4,674,326 A * 6/1987 Reinecke ................ F16D 66/00
188/1.11 L
5,189,391 A * 2/1993 Feldmann ............... B60T 17/22
340/453

(Continued)

FOREIGN PATENT DOCUMENTS

JP    S63-312044 A    12/1988
JP    H5-281104 A    10/1993
(Continued)

OTHER PUBLICATIONS

An Office Action; "Notice of Reasons for Rejection," issued by the Japanese Patent Office dated Nov. 6, 2018, which corresponds to Japanese Patent Application No. 2017-119277 and is related to U.S. Appl. No. 15/971,110.

*Primary Examiner* — Nimeshkumar D Patel
*Assistant Examiner* — Tania Courson
(74) *Attorney, Agent, or Firm* — Studebaker & Brackett PC

(57) ABSTRACT

An abnormal wearing detection device for seal members for detecting abnormal wearing of a seal member that slides in relation to a circumferential surface of a rotating member to seal the circumferential surface of the rotating member, includes: at least two measuring units among a load ratio measuring unit that measures a load ratio during rotation of the rotating member, a temperature measuring unit that measures the temperature of the seal member, and a gas concentration measuring unit that measures a concentration of a gas emitted from the seal member; and a determining unit that determines that abnormal wearing has occurred when it is detected that at least two measurement values measured by the at least two measuring units fail below a first reference value.

2 Claims, 4 Drawing Sheets

(51) Int. Cl.
*F16J 15/3296* (2016.01)
*F16J 15/00* (2006.01)
*F16C 17/02* (2006.01)
*G01N 3/56* (2006.01)
*G01M 3/00* (2006.01)
*G01M 13/00* (2019.01)
*F01D 21/12* (2006.01)
*F01D 25/18* (2006.01)

(52) U.S. Cl.
CPC ............ *G01M 13/005* (2013.01); *G01N 3/56* (2013.01); *F01D 21/12* (2013.01); *F01D 25/186* (2013.01); *G01M 3/002* (2013.01); *G01M 13/00* (2013.01)

(56) References Cited

U.S. PATENT DOCUMENTS

| | | | | |
|---|---|---|---|---|
| 5,540,448 A * | 7/1996 | Heinzen | ................... | F16J 15/16 |
| | | | | 116/208 |
| 6,003,872 A * | 12/1999 | Nord | .................... | F16J 15/3296 |
| | | | | 277/317 |
| 6,082,737 A * | 7/2000 | Williamson | ........ | G01M 13/005 |
| | | | | 277/317 |
| 6,615,954 B2 * | 9/2003 | Wirth | ...................... | F16D 66/00 |
| | | | | 188/1.11 E |
| 6,626,436 B2 * | 9/2003 | Pecht | ................... | F16J 15/3492 |
| | | | | 277/317 |
| 7,448,981 B2 * | 11/2008 | Mashiki | ................. | B60K 6/445 |
| | | | | 477/3 |
| 8,651,801 B2 * | 2/2014 | Shamseldin | .......... | F04D 29/124 |
| | | | | 415/112 |
| 9,221,395 B2 * | 12/2015 | Honig | ................. | B60C 23/0488 |
| 9,228,909 B1 * | 1/2016 | Rembisz | ............. | G01M 13/023 |
| 9,503,014 B2 * | 11/2016 | Mishima | ............... | H02P 29/028 |
| 9,541,199 B2 * | 1/2017 | Rust | ....................... | F16J 15/064 |
| 9,790,952 B2 * | 10/2017 | Shamseldin | .......... | F04D 29/124 |
| 9,819,300 B2 * | 11/2017 | Matsumoto | ............. | H02P 29/64 |
| 2003/0202188 A1 * | 10/2003 | Discenzso | ............... | B60C 11/24 |
| | | | | 356/477 |
| 2014/0204973 A1 * | 7/2014 | Kinoshita | ............. | G01K 13/00 |
| | | | | 374/152 |
| 2018/0287446 A1 * | 10/2018 | Mishima | ................. | H02K 15/12 |

FOREIGN PATENT DOCUMENTS

| | | | |
|---|---|---|---|
| JP | 2010-255845 A | 11/2010 | |
| WO | WO-0196765 A2 * | 12/2001 | ............ F04B 53/143 |

* cited by examiner

ABNORMAL WEARING DETECTION DEVICE FOR SEAL MEMBERS AND ROTOR DEVICE

This application is based on and claims the benefit of priority from Japanese Patent Application. No. 2017-119277, filed on 19 Jun. 2017, the content of which is incorporated herein by reference.

BACKGROUND OF THE INVENTION

Field of the Invention

The present invention relates to an abnormal wearing detection device for seal members and a rotor device having the same.

Related Art

A rotor device is widely used in a field of an industrial machine or the like. A rotor device has a rotating member (a rotor) rotatably accommodated in a housing and rotation of this rotor is controlled by a control device. Generally, in such a rotor device, an oil seal is provided between the rotor and the housing in order to prevent leakage of oil, grease, or the like enclosed in the housing and entrance of dust, water, or the like from the outside. The oil seal is a seal member that slides in relation to a circumferential surface of a rotating rotor to seal the circumferential surface.

Sliding of the oil seal in relation to the rotor is realized smoothly by a lubricant. However, when the lubricant decreases in amount or is exhausted, or when the oil seal is exposed to cutting liquid or the like, for example, and the resin of the oil seal softens, friction between the oil seal and the rotor may increase and abnormal wearing of the oil seal may occur. An abnormally worn oil seal may decrease in its sealing function and leakage of oil, grease, or the like and entrance of dust, water, or the like may occur. Due to this, conventionally, the temperature of an oil seal is measured to detect heat when the oil seal wears abnormally whereby the presence of abnormal wearing of the oil seal is detected (for example, see Patent Document 1).

Patent document 1: Japanese Unexamined Patent Application, Publication No. S63-312044

SUMMARY OF THE INVENTION

When the temperature of an oil seal is measured, the temperature resulting from heating when the oil seal wears abnormally may be measured or a stator may generate heat due to rotation of a rotor and the heat may be transferred to an oil seal and may be measured as heating of the oil seal. However, in a method of measuring the temperature of the oil seal, it is not possible to determine whether the measured temperature is the temperature resulting from heating occurring due to abnormal wearing of the oil seal or the temperature transferred to the oil seal due to the heat of a stator. Due to this, conventionally, there is a problem that an oil seal which does not need to be replaced is determined to be worn abnormally and is replaced unnecessarily. Furthermore, since a rotor device is stopped when an oil seal is replaced, operations stagnate unnecessarily and operation efficiency may decrease.

Therefore, an object of the present invention is to provide an abnormal wearing detection device for seal members capable of detecting abnormal wearing of a seal member that slides in relation to a rotating member to seal the circumferential surface more reliably. Another object of the present invention is to provide a rotor device capable of detecting abnormal wearing of a seal member that slides in relation to a rotating member to realize a sealing function more reliably.

(1) An abnormal wearing detection device according to the present invention is an abnormal wearing detection device (for example, an abnormal wearing detection device 4 to be described later) for seal members, for detecting abnormal wearing of a seal member (for example, an oil seal 24 to be described later) that slides in relation to a circumferential surface of a rotating member (for example, a rotor 22 to be described later) to seal the circumferential surface of the rotating member, including: at least two measuring units among a load ratio measuring unit (for example, a load ratio measuring unit 41 to be described later) that measures a load ratio during rotation of the rotating member, a temperature measuring unit (for example, a temperature measuring unit 42 to be described later) that measures the temperature of the seal member, and a gas concentration measuring unit (for example, a gas concentration measuring unit 43 to be described later) that measures a concentration of a gas emitted from the seal member; and a determining unit (for example, a determining unit 44 to be described later) that determines that abnormal wearing has occurred when it is detected that at least two measurement values measured by the at least two measuring units fall below a first reference value.

(2) In the abnormal wearing detection device according to (1), the determining unit may determine that abnormal wearing has occurred that it is determined that the at least two measurement values fall below the first reference value after reaching a second reference value higher than the first reference value.

(3) A rotor device (for example, a motor device 1 to be described later) according to the present invention is a rotor device (for example, a motor device 1 to be described later) in which a rotating member (for example, a rotor 22 to be described later) is rotatably accommodated in a housing (for example, a housing 21 to be described later), including: a seal member (for example, an oil seal 24 to be described later) that slides in relation to a circumferential surface of the rotating member to seal the circumferential surface of the rotating member; and the abnormal wearing detection device for seal members according to (1) or (2).

According to the present invention, it is possible to provide an abnormal wearing detection device for seal members capable of detecting abnormal wearing of a seal member that slides in relation to a rotating member to achieve a sealing function more reliably. According to the present invention, it is possible to provide a rotor device capable of detecting abnormal wearing of a seal member that slides in relation to a rotating member to realize a sealing function more reliably.

DETAILED DESCRIPTION OF THE INVENTION

Figure 1:
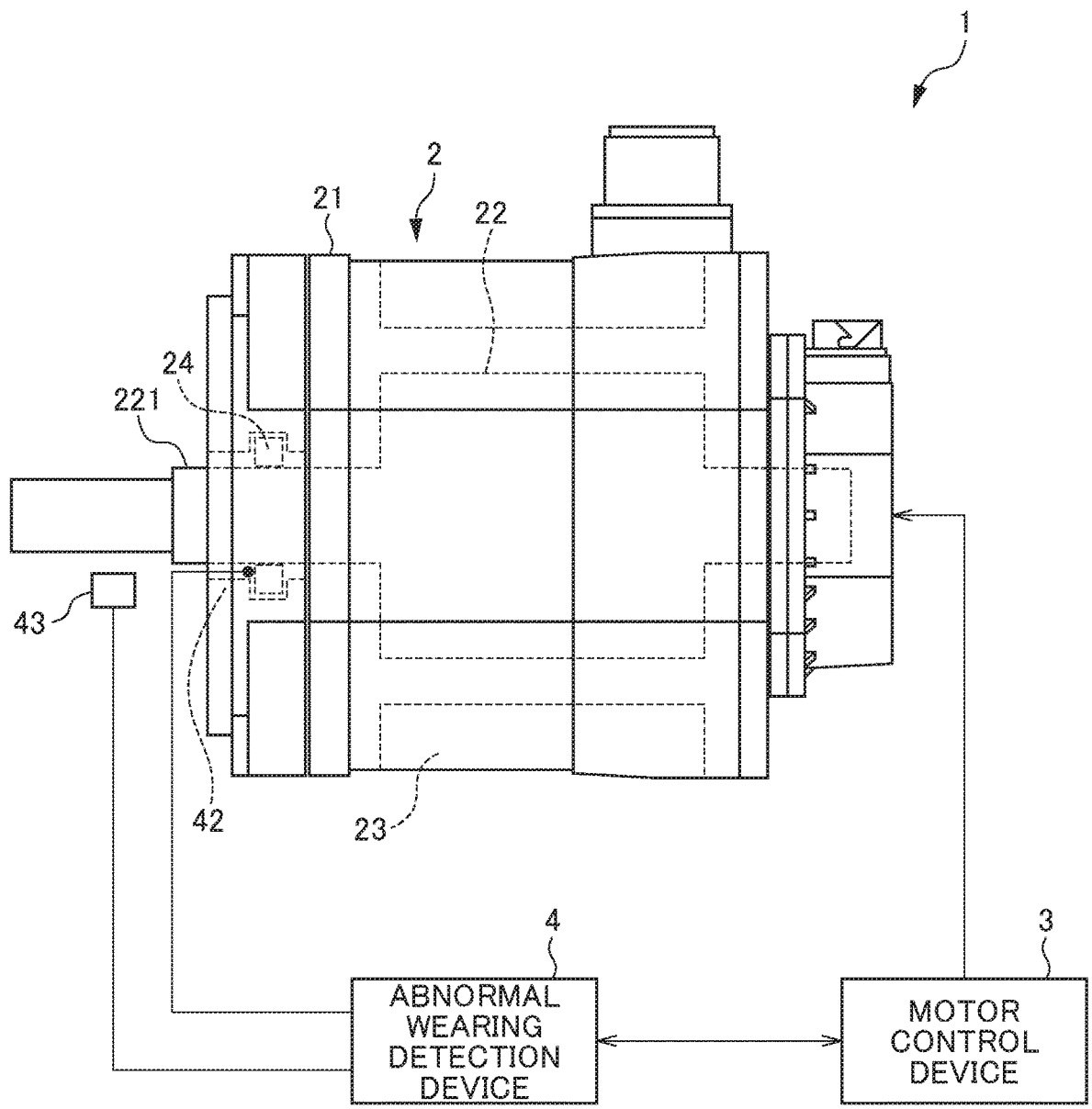
FIG. 1 is a diagram for describing an embodiment of rotor device having an abnormal wearing detection device for seal members according to the present invention.
Figure 2:
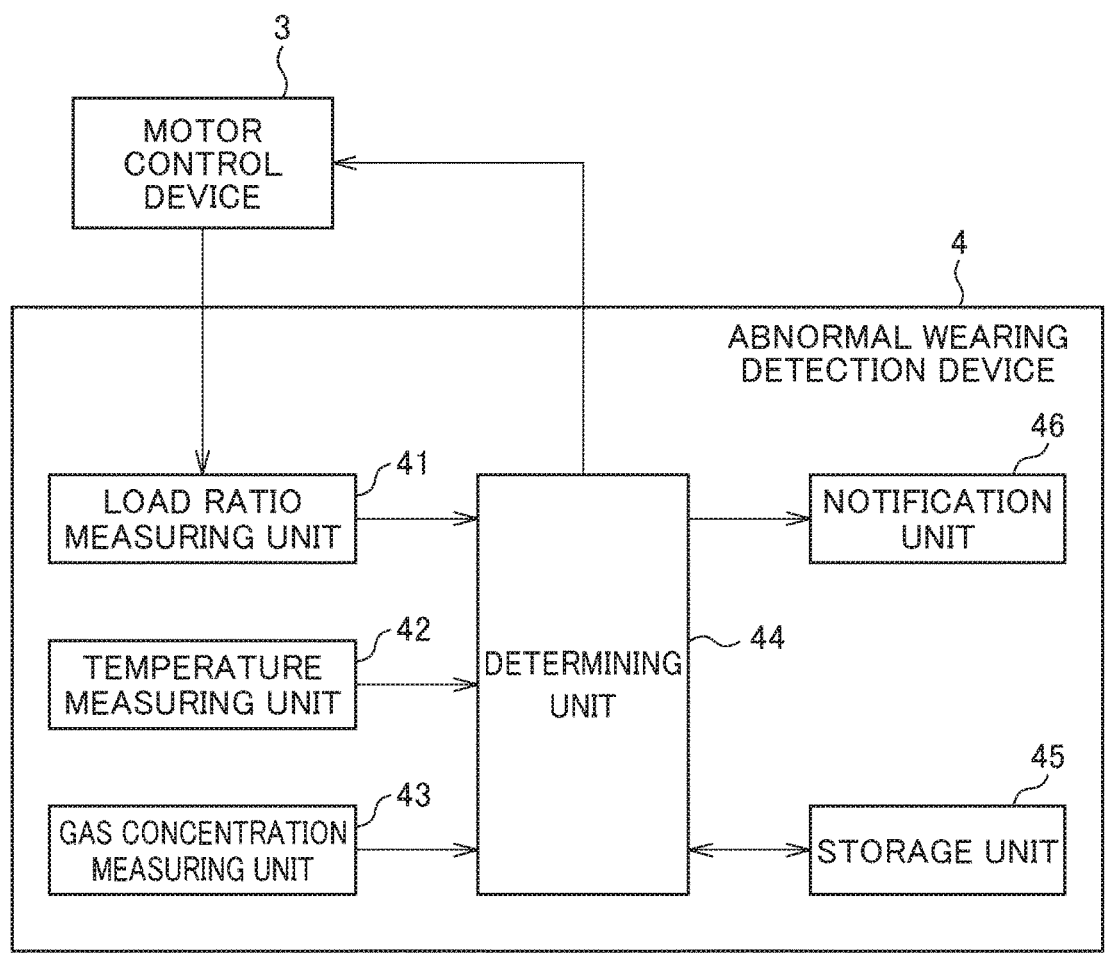
FIG. 2 is a block diagram for describing a configuration of an abnormal wearing detection device for seal members.

Hereinafter, an embodiment of the present invention will be described with reference to the drawings. FIG. 1 is a diagram for describing an embodiment of a rotor device having an abnormal wearing detection device for seal members according to the present invention. FIG. 2 is a block diagram for describing a configuration of an abnormal wearing detection device for seal members. In the present embodiment, a motor device 1 having a motor (an electric motor) 2 will be described as an example of a rotor device.

The motor device 1 according to the present embodiment includes a motor 2, a motor control device 3, and an abnormal wearing detection device 4. The motor 2 has a rotor 22 rotatably accommodated in a housing 21 and a stator 23 surrounding an outer circumference of the rotor. The stator 23 is fixed to an inner surface of the housing 21. When a predetermined driving current output from the motor control device 3 is applied to a coil of the stator 23, a rotating force is applied to the rotor 22 and the rotor 22 rotates.

An oil seal 24 is provided between the housing 21 and the rotor 22, specifically, between an inner circumferential surface of the housing 21 and an outer circumferential surface of a rotating shaft 221 of the rotor 22. The oil seal 24 according to the present embodiment is attached to an inner circumferential surface of the housing 21 and slides in relation to an outer circumferential surface of the rotating rotor 22 to thereby seal between the housing 21 and the rotor 22. The oil seal 24 is an example of a seal member according to the present invention.

In the present embodiment, an oil seal 24 provided at a distal end side (the left end side in the drawing) of the rotating shaft 221 of the rotor 22 is illustrated. Although an oil seal is also provided in a rear end side (the right end side in the drawing) of the rotating shaft 221, for example, the illustration of oil seals other than the oil seal 24 is omitted. Detection of abnormal wearing by an abnormal wearing detection device for seal members according to the present embodiment to be described later is applied to all oil seals provided in the motor 2.

The motor control device 3 performs control such as outputting a predetermined driving current to the stator 23 of the motor 2 to start driving of the motor 2 and stopping the output of the driving current to the stator 23 to stop driving of the motor 2. A current value of the driving current output from the motor control device 3 to the stator 23 is also output to the abnormal wearing detection device 4 to be described later.

As illustrated in FIG. 2, the abnormal wearing detection device 4 includes a load ratio measuring unit 41, a temperature measuring unit 42, a gas concentration measuring unit 43, a determining unit 44, a storage unit 45, and a notification unit 46. The load ratio measuring unit 41 receives a current value of a driving current of the motor 2 output from the motor control device 3 after driving of the motor 2 starts and measures a load ratio of the motor 2 from the current value.

Generally, in the motor 2, when the abnormal wearing of the oil seal 24 occurs due to a certain reason, the frictional resistance between the oil seal 24 and the rotor 22 increases, a torque varies, and a load increases. In this case, the driving current flowing into the motor 2 increases. The load ratio measuring unit 41 computes a load ratio from the current value of the driving current output from the motor control device 3. The load ratio is a ratio of a present torque (an actual torque) to a setting torque of the motor 2. A measurement value (the load ratio of the motor 2) measured by the load ratio measuring unit 41 is output to the determining unit 44.

The temperature measuring unit 12 is provided in contact with or in proximity to a lip portion, for example, of the oil seal 24 in the motor 2 to measure the temperature of the oil seal 24.

Although the temperature measuring unit 42 illustrated in FIG. 1 is disposed on the outer side of the oil seal 24, the temperature measuring unit 42 may be disposed on inner side of the oil seal 24 (inside the housing 21). The temperature measuring unit 42 is not particularly limited as long as it can measure the temperature of the oil seal 24 in the motor 2. In general, a thermocouple, a thermistor, or the like is used. The measurement value (the temperature of the oil seal 24) measured by the temperature measuring unit 42 is output to the determining unit 44.

The gas concentration measuring unit 43 measures the concentration of gas (outgas) emitted when the oil seal 24 slides in relation to the rotor 22 and a component such as rubber or a resin that forms the oil seal 24 gasifies.

Although the gas concentration measuring unit 43 illustrated in FIG. 1 is disposed outside the housing 21, the gas concentration measuring unit 43 may be disposed inside the housing 21. The gas concentration measuring unit 43 is disposed in proximity to the oil seal 24 even when the gas concentration measuring unit 43 is disposed outside or inside the housing 21. A specific example of the gas concentration measuring unit 43 is not particularly limited as long as the gas concentration measuring unit 43 can measure the concentration of the outgas from the oil seal 24. Generally, a gas sensor is used. The measurement value (outgas concentration) measured by the gas concentration measuring unit 43 is output to the determining unit 44.

The determining unit 44 determines the presence of abnormal wearing on the basis of the respective measurement values output from the load ratio measuring unit 41 temperature measuring unit 42 and the gas concentration measuring unit 43. As illustrated in FIG. 2, the determining unit 44 receives the respective measurement values including the load ratio of the motor 2 output from the load ratio measuring unit 41, the temperature of the oil seal 24 output from the temperature measuring unit 42, and the concentration of the outgas output from the gas concentration measuring unit 43. These measurement values are input to the determining unit 44 over time after operation of the motor 2 starts. The determining unit 44 monitors the changes over time in the respective measurement values every predetermined control period after the operation of the motor 2 starts, estimates the presence of abnormal wearing of the oil seal 24 for each measurement value, and determines the presence of abnormal wearing on the basis of the estimation result. The details of estimation and determination of abnormal wearing in the determining unit 44 will be described later.

The storage unit 45 stores reference values (a first reference value and a second reference value) of the respective measurement values of the load ratio of the motor 2, the temperature of the oil seal 24, and the concentration of the outgas in advance. This reference value is a value serving as a reference when the determining unit 44 estimates the presence of abnormal wearing of the oil seal 24 from the measurement values. The first and second reference values are larger than a normal value measured in advance in a state in which abnormal wearing does not occur in the oil seal 24 and the first reference value is set to be larger than the second reference value. That is, (second reference value)>(first reference value)>(normal value).

Figure 3:
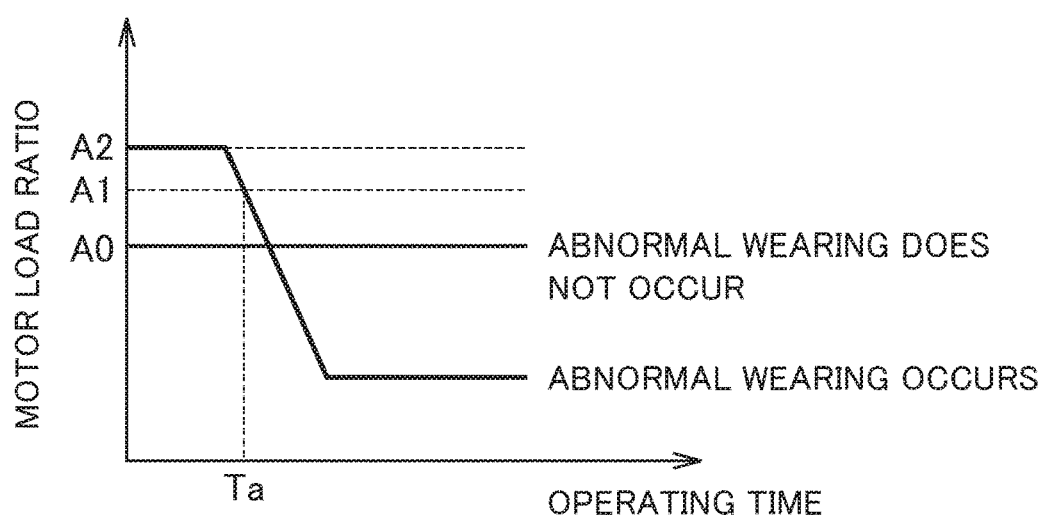
FIG. 3 is a graph illustrating a relation between a load ratio and an operating time of a motor.
Figure 4:
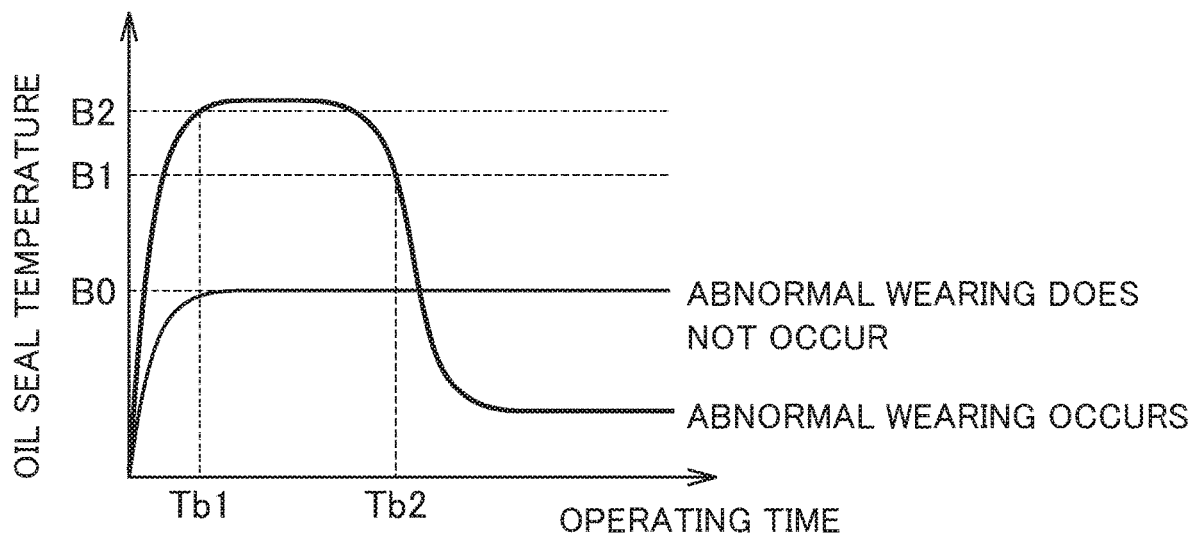
FIG. 4 is a graph illustrating a relation between the temperature and an operating time of an oil seal.
Figure 5:
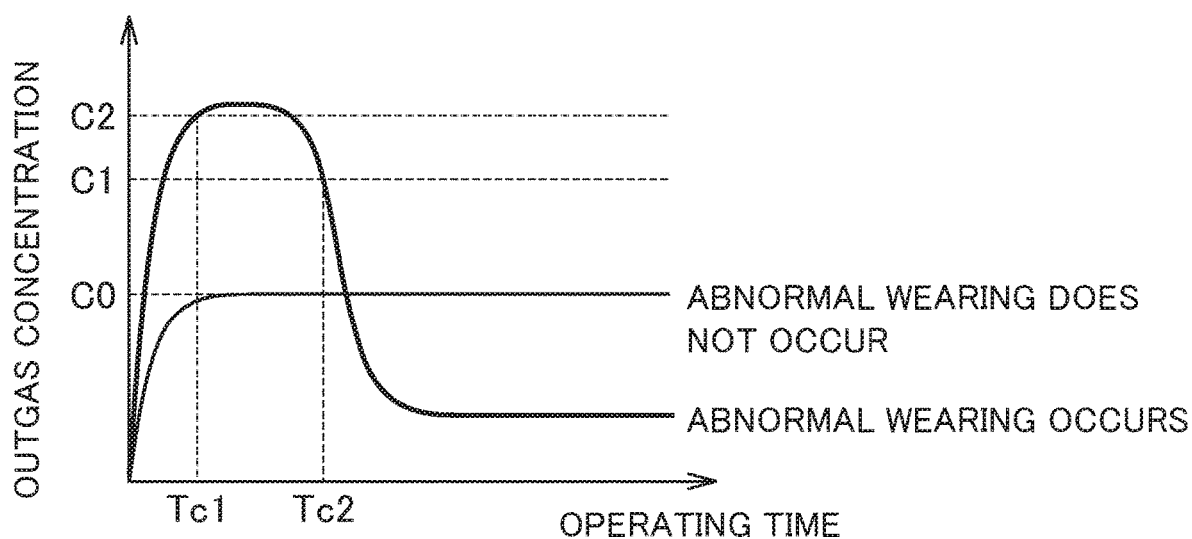
FIG. 5 a graph illustrating a relation between the concentration and an operating time of an outgas.

Here, a configuration in which the determining unit 44 estimates the presence of abnormal wearing on the basis of the respective measurement values will be described with reference to FIGS. 3 to 5. FIG. 3 is a graph illustrating a relation between a load ratio of the motor 2 and an operating time of the motor 2. FIG. 4 is a graph illustrating a relation between the temperature of the oil seal 24 and an operating time of the motor 2. FIG. 5 is a graph illustrating a relation between the concentration of outgas and an operating time of the motor

[Motor Load Ratio]

As illustrated in FIG. 3, the load ratio of the motor 2 has a value A0 (a normal value) that is substantially constant over time in a normal state in which abnormal wearing does not occur in the oil seal 24. In contrast, when abnormal wearing occurs in the oil seal 24, the frictional resistance between the oil seal 24 and the rotating shaft 221 of the rotor 22 increases and the load ratio has a large value. However, abnormal wearing of the oil seal 24 cannot be said to be the only cause of an increase in the load ratio. For example, a large load may be continuously applied to the rotor 22 depending on a use environment of the motor 2 and a high load ratio may be continued for a while. Therefore, it is not always reasonable to estimate that the oil seal 24 is worn abnormally immediately when a high load ratio is detected.

On the other hand, when the oil seal 24 is worn abnormally actually, although a load ratio higher than the normal value A0 is continued for a while similarly to the above-described case, the load ratio decreases abruptly after that. This is because abnormal wearing progresses, the oil seal 24 wears, and the pressing force with respect to the rotor 22 decreases. Therefore, from the viewpoint of reliability of abnormal wearing detection, it is preferable to estimate that the oil seal 24 worn abnormally when a decrease in the load ratio is detected.

Therefore, the determining unit 44 monitors a change over time in the load ratio of the motor 2 and detects whether the load ratio falls below a first reference value A1 set in advance in the storage unit 45 as illustrated in FIG. 3 every predetermined control period to thereby estimate the presence of abnormal wearing. That is, when abnormal wearing occurs, the load ratio of the motor 2 decreases due to wearing of the oil seal 24 and falls below the first reference value A1 at time Ta. Due to this, the determining unit 44 estimates that the oil seal 24 is worn abnormally after the elapse of time Ta.

The determining unit 44 of the present embodiment estimates that the oil seal 24 is worn abnormally when it is detected that the load ratio of the motor 2 falls below the first reference value A1 after the load ratio reaches a second reference value A2 higher than the first reference value A1. This is because the measurement value of the load ratio of the motor 2 when abnormal wearing occurs in the oil seal 24 varies in such a manner that the measurement value decreases abruptly due to wearing of the oil seal 24 after exhibiting a value higher than the normal value due to an increase in the frictional force of the oil seal 24. In this way, it is possible to eliminate the cause of a variation in the load ratio other than abnormal wearing as much as possible and to estimate the presence of abnormal wearing of the oil seal 24 more reliably from the measurement value of the load ratio of the motor 2.

A case in which "the load ratio of the motor 2 reaches the second reference value A2" includes a case in which the measurement value of the load ratio exceeds the second reference value A2 as well as a case in which the maximum value of the measurement value is the second reference value A2. Therefore, although the second reference value A2 illustrated in FIG. 3 is set to the same value as the maximum value of the varying load ratio, the second reference value A2 is not limited to the same value as the maximum value of the varying load ratio. The second reference value A2 may be set to a value higher than the first reference value A1 and a value equal to or smaller than the maximum value of the varying load ratio of the motor 2 expected when the abnormal wearing of the oil seal 24 occurs.

[Oil Seal Temperature]

As illustrated in FIG. 4, the temperature of the motor 2 has a value B0 (a normal value) that is substantially constant over time in a normal state in which abnormal wearing does not occur in the oil seal 24. In contrast, when abnormal wearing occurs in the oil seal 24, the temperature increases abruptly. However, the abnormal wearing of the oil seal 24 cannot be said to be the only cause of an increase in the temperature. For example, when the motor 2 may generate heat abnormally with rotation of the rotor 22, and the heat may be transferred to the oil seal 24 and be measured. Therefore, it is not always reasonable to estimate that the oil seal 24 is worn abnormally immediately when an increase in the temperature of the oil seal 24 is detected.

On the other hand, when the oil seal 24 is worn abnormally actually, although the temperature increases abruptly higher than the normal value B0 similarly to the above-described case, the temperature decreases after maintaining a peak value for a certain period. This is because abnormal wearing progresses, the oil seal 24 wears, the pressing force with respect to the rotor 22 decreases, and the friction decreases. Therefore, from the viewpoint of reliability of abnormal wearing detection, it is preferable to estimate that the oil seal 24 is worn abnormally when a decrease in the temperature of the oil seal 24 is detected.

Therefore, the determining unit 44 monitors a change over time in the temperature of the oil seal 24 and detects whether the temperature falls below a first reference value B1 set in advance in the storage unit 45 as illustrated in FIG. 4 every predetermined control period to thereby estimate the presence of abnormal wearing. That is, when abnormal wearing occurs, the temperature of the oil seal 24 decreases due to wearing of the oil seal 24 and falls below the first reference value B1 at time Tb2. Due to this, the determining unit 44 estimates that the oil seal 24 is worn abnormally after the elapse of time Tb2.

The determining unit 44 of the present embodiment estimates that the oil seal 24 is worn abnormally when it is detected that the temperature of the oil seal 24 falls below the first reference value B1 after the temperature reaches a second reference value B2 higher than the first reference value B1. That is, the measurement value of the temperature illustrated in FIG. 4 reaches the second reference value B2 at time Tb1 and falls below the first reference value B1 at time Tb2 after exceeding the second reference value B2. This is because the measurement value of the temperature when abnormal wearing occurs in the oil seal 24 varies in such a manner that the measurement value decreases abruptly due to wearing of the oil seal 24 after exhibiting a value higher than the normal value due to an increase in the frictional force of the oil seal 24. In this way, it is possible to eliminate the cause of a variation in the temperature other than abnormal wearing as much as possible and to estimate the presence of abnormal wearing of the oil seal 24 more reliably from the measurement value of the temperature of the oil seal 24.

A case in which "the temperature of the oil seal 24 reaches the second reference value B2" includes a case in which the measurement value of the temperature exceeds the second reference value B2 as well as a case in which the maximum value of the measurement value is the second reference value B2. Therefore, although the second reference value B2 illustrated in FIG. 4 is set to a value slightly lower than the maximum value of the varying temperature, the second reference value B2 is not limited to the value slightly lower than the maximum value of the varying temperature. The second reference value B2 may be set to a value higher than the first reference value B1 and a value equal to or smaller than the maximum value of the varying temperature of the oil seal 24 expected when the abnormal wearing of the oil seal 24 occurs.

[Outgas Concentration]

As illustrated in FIG. 5, the concentration of outgas from the oil seal 24 has a value C0 (a normal value) that is substantially constant over time in a normal state in which abnormal wearing does not occur in the oil seal 25. In contrast, when abnormal wearing occurs in the oil seal 21, the concentration increases abruptly. However, the abnormal wearing of the oil seal 24 cannot be said to be the only cause of an increase in the outgas concentration. For example, the temperature of the oil seal 24 may increase due to an increase in a use environmental temperature and the heating of the motor 2 and outgas may increase temporarily. Therefore, it is not always reasonable to estimate that the oil seal 24 is worn abnormally immediately when an increase in the concentration of the outgas is detected.

On the other hand, when the oil seal 24 is worn abnormally, although the concentration of the outgas increases abruptly higher than a normal value C0 similarly to the above-described case, the concentration of the outgas decreases after maintaining a peak value for a certain period. This is because abnormal wearing progresses, the oil seal 24 wears, the pressing force with respect to the rotor 22 decreases, and the friction decreases. Therefore, from the viewpoint of reliability of abnormal wearing detection, it is preferable to estimate that the oil seal 24 is worn abnormally when a decrease in the concentration of the outgas from the oil seal 24 is detected.

Therefore, the determining unit 44 monitors a change over time in the concentration of the outgas from the oil seal 24 and detects whether the concentration of the outgas falls below a first reference value C1 set in advance in the storage unit 45 as illustrated in FIG. 5 every predetermined control period to thereby estimate the presence of abnormal wearing. That is, when abnormal wearing occurs, the concentration of the outgas decreases due to wearing of the oil seal 24 and falls below the first reference value C1 at time Tc2. Due to this, the determining unit 44 estimates that the oil seal 24 is worn abnormally after the elapse of time Tc2.

The determining unit 44 of the present embodiment estimates that the oil seal 24 is worn abnormally when it is detected that the concentration of the outgas falls below the first reference value C1 after the concentration reaches a second reference value C2 higher than the first reference value C1. That is, the measurement value of the outgas concentration illustrated in FIG. 5 reaches the second reference value C2 at time Tc1 and falls below the first reference value C1 at time Tc2 after exceeding the second reference value C2. This is because the measurement value of the outgas concentration when abnormal wearing occurs in the oil seal 24 varies in such a manner that the measurement value decreases abruptly due to wearing of the oil seal 24 after exhibiting a value higher than the normal value due to an increase in the frictional force of the oil seal 24. In this way, it is possible to eliminate the cause of a variation in the outgas concentration other than abnormal wearing as much as possible and to estimate the presence of abnormal wearing of the oil seal 24 more reliably from the measurement value of the outgas concentration.

A case in which "the outgas concentration reaches the second reference value C2" includes a case in which the measurement value of the outgas concentration exceeds the second reference value C2 as well as a case in which the maximum value of the measurement value is the second reference value C2. Therefore, although the second reference value C2 illustrated in FIG. 5 is set to a value slightly lower than the maximum value of the varying outgas concentration, the second reference value C2 is not limited to the value slightly lower than the maximum value of the varying outgas concentration. The second reference value C2 may be set to a value higher than the first reference value C1 and a value equal to or smaller than the maximum value of the varying outgas concentration expected when the abnormal wearing or the oil seal 24 occurs.

As described above, the determining unit 44 monitors whether the measurement values of the load ratio of the motor 2, the temperature of the oil seal 24, and the outgas concentration fall below the first reference values A1, B1, and C1 and individually estimates the presence of abnormal wearing when the measurement values fall below the first reference values. However, the individual estimation is temporary and is not a final decision. The determining unit 44 determines that the oil seal 24 is worn abnormally when it is estimated that the oil seal 24 is worn abnormally in at least two measurement values from the estimation results of the presence of abnormal wearing based on the three measurement values. This determination is the final decision of the determining unit 44.

Here, even when it is estimated that abnormal wearing has occurred in two measurement values only as well as when it is estimated that abnormal wearing has occurred in all three measurement values, the determining unit 44 determines that the oil seal 24 is worn abnormally. This is because, when it is estimated that abnormal wearing has occurred in two measurement values, it is estimated with a high probability that the oil seal 24 has left a normal state and started wearing abnormally.

The determining unit 44 outputs a determination signal to a notification unit 46 when it is determined that the oil seal 24 is worn abnormally.

The determination signal output from the determining unit 44 to the notification unit 46 is not limited to one type only. For example, the urgency level when it is estimated that abnormal wearing has occurred in two measurement values only may be lower than the urgency level when it is estimated that abnormal wearing has occurred in all three measurement values. Therefore, the determining unit 44 may output a determination signal to the notification unit 46 in such a manner that a determination signal output when it is estimated that the oil seal 24 is worn abnormally in all three measurement values is distinguished from the determination signal output when it is estimated that the oil seal 24 is worn abnormally in two measurement values.

In this case, the determining unit 44 may output a warning signal as the determination signal to be output to the notification unit 46 when it is estimated that the oil seal 24 is worn abnormally in all three measurement values and may output a caution signal having a lower warning level than the warning signal as a determination signal output to the notification unit 46 when it is estimated that the oil seal 24 is worn abnormally in two measurement values only. By sending a notification of caution to an operator via the caution signal, the operator can take measures such as visually observing the state of the oil seal 24 of the motor 2. As a result, for example, when the operator determines that replacement or the like of the oil seal 24 is not necessary at the present time point, the operator can avoid stagnation of operations by continuously operating the motor 2 until the determining unit 44 outputs a warning signal.

When it is determined that the oil seal 24 is worn abnormally from all three measurement values, the determining unit 44 may output a motor stop command for stopping the operation of the motor 2 to the motor control device 3 in order to prevent damage or the like of the motor 2 due to malfunction of the oil seal 24.

The notification unit 46 notifies the operator of abnormal wearing of the oil seal 24 on the basis of the determination signal output from the determining unit 44. A specific notification method of the notification unit 46 is not particularly limited, and for example, a notification based on a warning sound such as a buzzer sound or a chime, a notification based on a voice, a notification based on turning on and off of a lamp, a notification based on a screen display on a monitor, and the like may be used. The notification unit 46 output any one of these notifications and may output a combination of two or more notifications.

When the warning signal and the caution signal are output from the determining unit 44 as the determination signal in a distinguished manner, the notification unit 46 may output a notification of warning based on the warning signal and a notification of caution based on the caution signal to the operator in a distinguished manner in such a way that a red lamp is turned on for the warning signal and a yellow lamp is turned on for the caution signal, for example.

Figure 6:
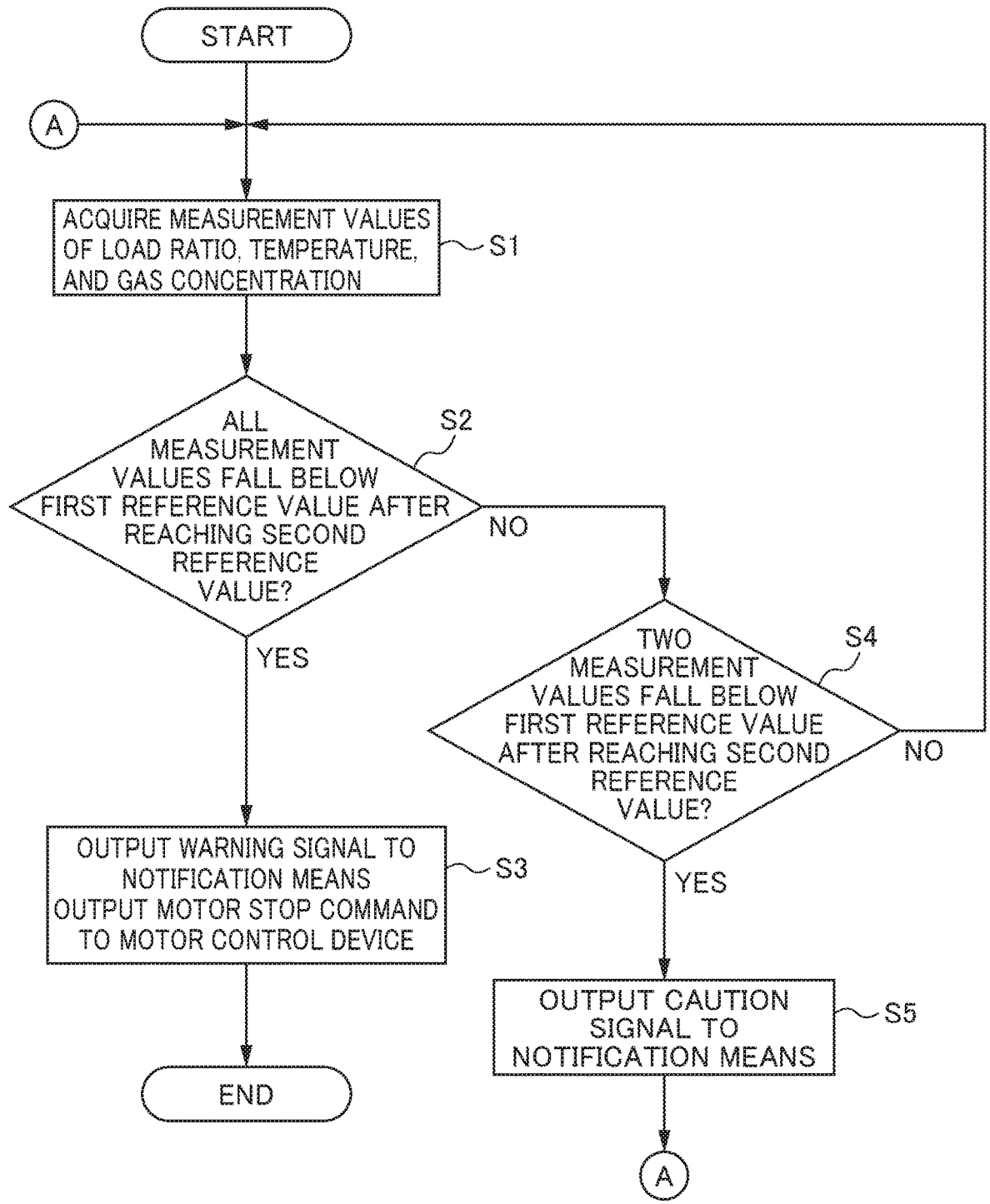
FIG. 6 is a flowchart for describing a specific control example of an abnormal wearing detection device.

Next, an example of specific control of the abnormal wearing detection device 4 provided in the motor device 1 will be described with reference to the flowchart illustrated in FIG. 6. In step S1, after operation of the motor 2 starts, the determining unit 44 of the abnormal wearing detection device 4 acquires three measurement values measured by the load ratio measuring unit 41, the temperature measuring unit 42, and the gas concentration measuring unit 43 over time.

In step S2, the determining unit 44 compares the acquired three measurement values with the first and second reference values for each measurement value set in the storage unit 45 every predetermined control period. On the basis of the comparison result, the determining unit 44 determines whether each of the three measurement values falls below the first reference value after reaching the second reference value and estimates the presence of abnormal wearing of the oil seal 24.

When it is estimated that the oil seal 24 is worn abnormally in all three measurement values (step S2: Yes), the determining unit 44 determines that the oil seal 24 is worn abnormally and outputs a warning signal to the notification unit 46 and a motor stop command to the motor control device 3 in step S3. In this way, the notification unit 46 notifies the operator of the occurrence of abnormal wearing of the oil seal 24 in order to warn the operator. The motor control device 3 stops supplying a driving current to the motor 2 on the basis of the motor stop command output from the abnormal wearing detection device 4 and stops operation of the motor 2.

On the other hand, in step S2, when it is estimated that the oil seal 24 is not worn abnormally in all three measurement values (step S2: No), the determining unit 44 determines whether it is estimated that the oil seal 24 is worn abnormally from the fact that two measurement values fall below the first reference value after reaching the second reference value in step S4.

When it is estimated that the oil seal 24 is worn abnormally in two measurement values (step S4: Yes), the determining unit 44 determines that the oil seal 24 is worn abnormally and outputs a caution signal to the notification unit 45 in step S5. In this way, the notification unit 46 notifies the operator of the fact that the oil seal 24 is worn abnormally or starts wearing abnormally to prompt the operator to take measures such as checking the state of the oil seal 24. After that, the processes starting from step S1 are repeated.

When it is estimated in step S4 that the oil seal 24 is not worn abnormally from any measurement value and the oil seal 24 is worn abnormally from only one measurement value, the determining unit 44 outputs a determination result of "No" and the processes starting from step S1 are repeated. That is, the determining unit 44 determines that the oil seal 24 is not worn abnormally. This is because there is a cause of a variation in the measurement value other than the abnormal wearing of the oil seal 24. Therefore, it is possible to prevent unnecessary replacement of the oil seal 24 which does not need replacement.

In this way, the abnormal wearing detection device 4 and the motor device 1 having the same according to the present invention can detect abnormal wearing more reliably than the conventional technique on the basis of a combination of estimation results of the presence of abnormal wearing of the oil seal 24 based on three measurement values. Therefore, a detection error of abnormal wearing is prevented more reliably, a situation in which an oil seal which does not need replacement is replaced unnecessarily is avoided, stagnation of operations resulting from unnecessary stopping of the motor 2 for replacement of the oil seal 24 does not occur, and a decrease in operation efficiency is avoided.

The determining unit 44 of the abnormal wearing detection device 4 according to the present invention may determine that abnormal wearing has occurred when it is detected that at least two measurement values measured by at least two measuring units of the load ratio measuring unit 41, the temperature measuring unit 42, and the gas concentration measuring unit 43 fall below the first reference values A1, B1, and C1.

In the above-described embodiment, the motor device 1 having the motor 2 has been described as an example of a rotor device. However, the rotor device is not limited to the motor device. The rotor device of the present invention can be widely applied to a rotor device in which a rotating member is rotatably accommodated in a housing and which includes a seal member that slides in relation to a circumferential surface of the rotating member to seal the circumferential surface of the rotating member.

The seal member of the present invention is not limited to the oil seal illustrated in the embodiment. The present invention can be widely applied to a seal member that slides in relation to a circumferential surface of a rotating member to seal the circumferential surface of the rotating member.

In the above-described embodiment, a seal member (the oil seal 24) that slides in relation to the outer circumferential surface of a rotating member (the rotor 22) to seal the outer circumferential surface has been described. However, the seal member may slide in relation to an inner circumferential surface of a rotating member to seal the inner circumferential surface.

The abnormal wearing detection device 4 of the present invention may be provided inside the housing 21 of the motor 2 and may be attached to an outer portion of the housing 21. The abnormal wearing detection device 4 except the temperature measuring unit 42 and the gas concentration measuring unit 43 may be provided in the motor control device 3.

EXPLANATION OF REFERENCE NUMERALS

1: Motor device (Rotor device)
2: Motor
21: Housing
22: Rotor (Rotating member)
24: Oil seal (Seal member)
4: Abnormal wearing detection device
41: Load ratio measuring unit
42: Temperature measuring unit
43: Gas concentration measuring unit
44: Determining unit

What is claimed is:

1. An abnormal wearing detection device for oil seals, for detecting abnormal wearing of an oil seal that slides in relation to a circumferential surface of a rotating member to seal the circumferential surface of the rotating member, comprising:
   a load ratio measuring unit that measures a load ratio during rotation of the rotating member;
   a temperature measuring unit that measures the temperature of the oil seal;
   a gas concentration measuring unit that measures a concentration of a gas emitted from the oil seal; and
   a determining unit that determines that abnormal wearing has occurred when it is detected that at least two measurement values of measurement values measured by the load ratio measuring unit, the temperature measuring unit, and the gas concentration measuring unit fall below a first reference value after reaching a second reference value, as a result of comparing each of the measurement values with the first reference value higher than a normal value and the second reference value higher than the first reference value.

2. A rotor device in which the rotating member is rotatably accommodated in a housing, comprising:
   the oil seal that slides in relation to a circumferential surface of the rotating member to seal the circumferential surface of the rotating member; and
   the abnormal wearing detection device for oil seals according to claim 1.

* * * * *